United States Patent
Zieger et al.

(10) Patent No.: US 12,295,660 B2
(45) Date of Patent: May 13, 2025

(54) MULTI-VIEW CORNEAL TOPOGRAPHER

(71) Applicant: Alcon Inc., Fribourg (CH)

(72) Inventors: Peter Zieger, Berlin (DE); Martin Gründig, Rangsdorf (DE); Daniil Nekrassov, Berlin (DE); Horia Grecu, Berlin (DE)

(73) Assignee: ALCON INC., Fribourg (CH)

( * ) Notice: Subject to any disclaimer, the term of this patent is extended or adjusted under 35 U.S.C. 154(b) by 560 days.

(21) Appl. No.: 17/649,560

(22) Filed: Feb. 1, 2022

(65) Prior Publication Data
US 2022/0248951 A1 Aug. 11, 2022

Related U.S. Application Data

(60) Provisional application No. 63/146,837, filed on Feb. 8, 2021.

(51) Int. Cl.
| | |
|---|---|
| *A61B 3/107* | (2006.01) |
| *A61B 3/00* | (2006.01) |
| *A61B 3/14* | (2006.01) |
| *G06T 7/64* | (2017.01) |
| *G06T 15/06* | (2011.01) |

(52) U.S. Cl.
CPC ............ *A61B 3/107* (2013.01); *A61B 3/0008* (2013.01); *A61B 3/14* (2013.01); *G06T 7/64* (2017.01); *G06T 15/06* (2013.01); *G06T 2207/30041* (2013.01)

(58) Field of Classification Search
CPC ......... A61B 3/107; A61B 3/0008; A61B 3/14; A61B 3/0025; A61B 3/13; G06T 7/64; G06T 15/06; G06T 2207/30041
USPC ......................................................... 351/206
See application file for complete search history.

(56) References Cited

U.S. PATENT DOCUMENTS

| | | | |
|---|---|---|---|
| 5,847,804 A | 12/1998 | Sarver et al. | |
| 5,886,767 A | 3/1999 | Snook | |
| 6,692,126 B1 | 2/2004 | Xie et al. | |
| 2002/0154269 A1 | 10/2002 | Liu | |
| 2006/0158612 A1 | 7/2006 | Polland et al. | |
| 2006/0228011 A1* | 10/2006 | Everett | A61B 3/113 382/128 |
| 2007/0282313 A1 | 12/2007 | Huang | |

(Continued)

FOREIGN PATENT DOCUMENTS

EP        1038494 A1        9/2000

*Primary Examiner* — Mohammed A Hasan (57) ABSTRACT

An ophthalmic system for generating a topography of an anterior corneal surface of an eye comprises an illuminator, cameras, and a computer. The illuminator illuminates the anterior corneal surface of the eye with a Placido pattern, which reflects the Placido pattern. Each camera generates an image of the reflected Placido pattern to yield multiple images. At least one camera is oriented off an axis of the eye. For each image, the computer calculates a curvature value for each data point of the image, where a data point corresponds to a surface point of the anterior corneal surface. The calculations yield curvature values for each surface point. The computer determines the curvature at each surface point from one or more curvature values for the surface point. The computer generates the topography of the anterior corneal surface from the curvatures at the surface points of the anterior corneal surface.

18 Claims, 6 Drawing Sheets

(56) References Cited

U.S. PATENT DOCUMENTS

| | | | |
|---|---|---|---|
| 2011/0015541 A1* | 1/2011 | Padrick | A61B 3/10 |
| | | | 600/558 |
| 2015/0131055 A1 | 5/2015 | Catanzariti et al. | |
| 2016/0302971 A1* | 10/2016 | Morley | G16H 40/20 |
| 2018/0092534 A1 | 4/2018 | Nabhan | |
| 2019/0335995 A1* | 11/2019 | Dhadwal | A61B 3/1225 |
| 2019/0357767 A1* | 11/2019 | Nekrassov | A61B 3/14 |
| 2020/0188166 A1* | 6/2020 | Buck | A61F 9/00825 |

* cited by examiner

MULTI-VIEW CORNEAL TOPOGRAPHER

TECHNICAL FIELD

The present disclosure relates generally to corneal topographers, and more particularly to a multi-view corneal topographer.

BACKGROUND

Reflection-based corneal topographers are used to determine the shape of the anterior corneal surface. A topographer projects a pattern (e.g., concentric rings or grid of dots) onto the anterior corneal surface and analyzes the reflection of the pattern to determine the shape of the surface. If the surface is an ideal sphere, the reflected pattern matches the projected pattern. If the surface has variations, areas where the reflected portions of the pattern (e.g. rings or dots) are closer together indicate steeper corneal curvature, and areas where the portions are farther part indicate flatter areas. In addition, distinct, well-formed portions indicate that the corneal surface is smooth.

In certain situations, however, known topographers do not provide satisfactory images. For example, certain topographers fail to provide detailed information along specific directions of the pattern or around the apex of the eye. In addition, the illumination systems of certain topographers cannot illuminate a sufficient area of the cornea, which limits the corneal coverage of the topographer.

BRIEF SUMMARY

In certain embodiments, an ophthalmic system for generating a topography of an anterior corneal surface of an eye comprises an illuminator, cameras, and a computer. The illuminator illuminates the anterior corneal surface of the eye with a Placido pattern, which reflects the Placido pattern. The eye has an axis. Each camera generates an image of the reflected Placido pattern to yield multiple images. At least one camera is oriented off the axis of the eye. The computer receives the images from the cameras. For each image, the computer calculates a curvature value for each data point of multiple data points of the image. Each data point of the image corresponds to a surface point of multiple surface points of the anterior corneal surface. The calculations yield curvature values for each surface point. For each surface point, the computer determines the curvature at the surface point from one or more curvature values for the surface point. The computer generates the topography of the anterior corneal surface from the curvatures at the surface points of the surface points of the anterior corneal surface.

Embodiments may include none, one, some, or all of the following features: The curvature value for a data point is a normal vector representing a surface normal at the surface point corresponding to the data point. For each image, the computer calculates the curvature value for each data point by determining there is a deviation between an expected Placido pattern and the reflected Placido pattern at the data point, and adjusting a normal vector for the data point according to the deviation. For each image, the computer calculates the curvature value for each data point by: determining there is a deviation between an expected Placido pattern and the reflected Placido pattern at the data point; if the deviation indicates a steeper curvature, adjusting a normal vector for the data point to represent the steeper curvature; and if the deviation indicates a flatter curvature, adjusting the normal vector for the data point to represent the flatter curvature. For each surface point, the computer determines the curvature at the surface point from one or more curvature values for the surface point by determining the curvature at the surface point from a function of the curvature values for the surface point. The function may be an average, e.g., a weighted average, of the curvature values for the surface point. For each surface point, the computer determines the curvature at the surface point from one or more curvature values for the surface point by applying a ray-tracing procedure to determine the curvature at the surface point. The ray-tracing procedure may be applied by: defining rays, each ray traced from an illuminator element of the illuminator, to the anterior corneal surface, and to a camera, each ray described by ray parameters, each ray parameter having a value; optimizing the values of the ray parameters according to constraints, the constraints comprising the curvature values for the surface points; and determining the curvature at a surface point from the optimized values of the ray parameters.

In certain embodiments, a method for generating a topography of an anterior corneal surface of an eye comprises: illuminating, by an illuminator, the anterior corneal surface of the eye with a Placido pattern, the eye having an axis, the anterior corneal surface reflecting the Placido pattern; generating, by multiple cameras, multiple images of the reflected Placido pattern, at least one camera oriented off the axis of the eye; receiving, by a computer, the images from the cameras; for each image, calculating, by the computer, a curvature value for each data point of multiple data points of the image, each data point of the image corresponding to a surface point of multiple surface points of the anterior corneal surface, the calculations yielding curvature values for each surface point; for each surface point, determining, by the computer, the curvature at the surface point from one or more curvature values for the surface point; and generating, by the computer, the topography of the anterior corneal surface from the curvatures at the surface points of the anterior corneal surface.

Embodiments may include none, one, some, or all of the following features: The curvature value for a data point is a normal vector representing a surface normal at the surface point corresponding to the data point. For each image, the computer calculates the curvature value for each data point by determining there is a deviation between an expected Placido pattern and the reflected Placido pattern at the data point, and adjusting a normal vector for the data point according to the deviation. For each image, the computer calculates the curvature value for each data point by: determining there is a deviation between an expected Placido pattern and the reflected Placido pattern at the data point; if the deviation indicates a steeper curvature, adjusting a normal vector for the data point to represent the steeper curvature; and if the deviation indicates a flatter curvature, adjusting the normal vector for the data point to represent the flatter curvature. For each surface point, the computer determines the curvature at the surface point from one or more curvature values for the surface point by determining the curvature at the surface point from a function of the curvature values for the surface point. The function may be an average, e.g., a weighted average, of the curvature values for the surface point. For each surface point, the computer determines the curvature at the surface point from one or more curvature values for the surface point by applying a ray-tracing procedure to determine the curvature at the surface point. The ray-tracing procedure may be applied by: defining rays, each ray traced from an illuminator element of the illuminator, to the anterior corneal surface, and to a camera, each ray described by ray parameters, each ray parameter having a value; optimizing the values of the ray parameters according to constraints, the constraints comprising the curvature values for the surface points; and determining the curvature at a surface point from the optimized values of the ray parameters.

In certain embodiments, an ophthalmic system for generating a topography of an anterior corneal surface of an eye comprises an illuminator, cameras, and a computer. The illuminator illuminates the anterior corneal surface of the eye with a Placido pattern, which reflects the Placido pattern. The eye has an axis. Each camera generates an image of the reflected Placido pattern to yield multiple images. At least one camera is oriented off the axis of the eye. The computer receives the images from the cameras. For each image, the computer calculates a curvature value for each data point of multiple data points of the image. Each data point corresponds to a surface point of multiple surface points of the anterior corneal surface. The calculations yield curvature values for each surface point. The curvature value for a data point is a normal vector representing a surface normal at the surface point corresponding to the data point. A curvature value is calculated for each data point by: determining there is a deviation between an expected Placido pattern and the reflected Placido pattern at the data point; if the deviation indicates a steeper curvature, adjusting a normal vector for the data point to represent the steeper curvature; and if the deviation indicates a flatter curvature, adjusting the normal vector for the data point to represent the flatter curvature. For each surface point, the computer determines the curvature at the surface point from one or more curvature values for the surface point. The curvature at the surface point is determined from a weighted average of the curvature values for the surface point or by applying a ray-tracing procedure to determine the curvature at the surface point. The computer generates the topography of the anterior corneal surface from the curvatures at the surface points of the anterior corneal surface.

BRIEF DESCRIPTION OF THE DRAWINGS

FIGS. 2 and 3 illustrate how cameras of the system of FIG. 1 may provide image data for determining the curvature of an anterior corneal surface, where

FIGS. 5 and 6 illustrate an example of a method for applying ray-tracing to determine the shape of anterior corneal surface, which may be performed by the system of FIG. 1, where FIG. 6 illustrates the example of the method for applying ray-tracing.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain embodiments, a system illuminates the anterior corneal surface with a Placido pattern, which reflects the Placido pattern. Multiple cameras generate images of the reflected Placido pattern from different viewpoints. Images from different viewpoints provide more information than an image from just one viewpoint. Information from the multiple images is used to generate a topography of the anterior corneal surface.

Figure 1:
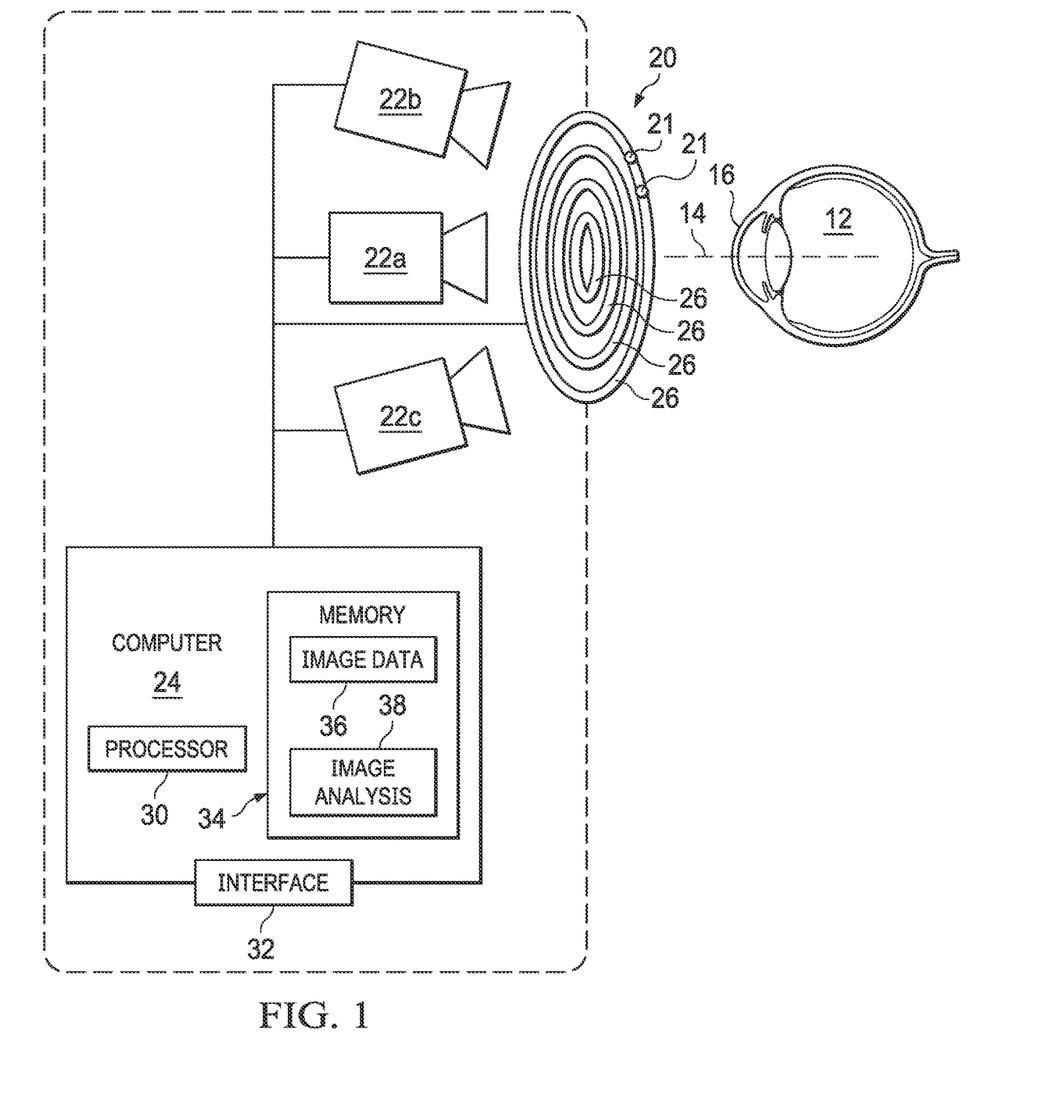
FIG. 1 illustrates an example of a diagnostic ophthalmic system for determining the topography of the anterior corneal surface of an eye, according to certain embodiments.

FIG. 1 illustrates an example of a diagnostic ophthalmic system 10 for determining the topography of the anterior corneal surface 16 of an eye 12, according to certain embodiments. In the example, system 10 includes an illuminator 20, a plurality of cameras 22 (22a-22c), and a computer 24. Illuminator 20 includes illuminator rings 26, which may have illuminator elements 21. Computer 24 includes one or more processors 30, an interface 32, and a memory 34. Memory 34 stores data (e.g., image data 36) and applications (e.g., image analysis module 38).

As an overview of operation, illuminator 20 illuminates anterior corneal surface 16 with a Placido pattern. Anterior corneal surface 16 reflects the Placido pattern. Cameras 22 generate images of the reflected Placido pattern from different viewpoints. Computer 24 analyzes the images to generate a topography of anterior corneal surface 16. In certain embodiments, computer 24 calculates curvature values for the data points of the images from cameras 22, where a data point corresponds to a surface point of anterior corneal surface 16. Computer 24 then determines the curvature at the surface points from the curvature values corresponding to the surface point.

Turning to the parts of system 10, illuminator 20 illuminates anterior corneal surface 16 with a pattern, e.g. a Placido pattern. "Placido pattern" may refer to any suitable pattern of shapes that can be used to detect corneal aberrations. Examples of Placido patterns include: (1) concentric rings, of the same or different thicknesses, equally or unequally spaced; (2) a grid of dots, of the same or different sizes, equally or unequally spaced; and (3) a series of lines, of the same or different thicknesses, equally or unequally spaced.

Illuminator 20 may comprise any suitable arrangement of one or more light sources configured to illuminate corneal surface 16 with the pattern. In certain embodiments that use a Placido pattern, illuminator 20 includes illuminator rings 26, where each illuminator ring 26 illuminates corneal surface 16 with a ring of the Placido pattern. In some embodiments, illuminator 20 includes illuminator elements 21, such as pixel illuminators, where each pixel illuminates corneal surface 16 with a pixel of light. The pixels are combined to yield the pattern. Computer 24 may turn on and off particular pixel illuminators to yield a specific pattern.

Anterior corneal surface 16 of eye 12 typically has a tear film. The tear film-air interface reflects the Placido pattern. The reflected Placido pattern can indicate the shape of corneal surface 16. If the surface is an ideal sphere, the reflected pattern matches the projected pattern. If the surface has aberrations, areas where the reflected portions of the pattern (e.g., rings or dots) are closer together indicate steeper corneal curvature, and areas where the portions are farther part indicate flatter curvature.

Camera 22 generates an image of the reflected Placido pattern. Camera 22 may be any suitable camera that captures and records images. For example, camera 22 may be a digital camera that records the image as digital image data. Camera 22 may include: an image sensor that detects light reflected from an object, such as a digital image sensor (e.g., CCD or CMOS); an image processor that converts the sensor output to digital image data representing the image; and a memory that records the image as image data 36.

System 10 may have any suitable number (e.g., two, three, or more) and arrangement of cameras. In the example, camera 22a is an on-axis camera, where the optical axis of camera 22a substantially coincides with an axis 14 (e.g., optical or visual) of eye 12. Cameras 22b-c are off-axis cameras, where the optical axis of each camera 2b-c is at an angle with an axis of eye 12. The angle may have any suitable value, e.g., a value within the range of 1 to 10, 10 to 30, 30 to 40, or 40 to 60 degrees. In other examples, cameras 22 may be all off-axis cameras or may include an on-axis camera. In certain embodiments, system 10 may include off-axis cameras that can be installed onto a system with existing on-axis instruments. In certain embodiments, system 10 may include only one camera 22 that moves to different positions (e.g., on-axis and/or off-axis) to operate as different cameras 22.

Computer 24 determines the topography of corneal surface 16 from the images of the reflected Placido pattern. In certain embodiments, computer 24 calculates a curvature value for the data points of the images, where a data point corresponds to a surface point of anterior corneal surface. Computer 24 then determines the curvature at the surface points from the curvature values corresponding to the surface point.

Computer 24 may calculate curvature values for the data points of an image in any suitable manner. In certain embodiments, a curvature value for a data point is a normal vector representing the surface normal at the surface point corresponding to the data point. In the embodiments, computer 24 determines there is a deviation between an expected Placido pattern and the reflected Placido pattern at the point, and adjusts the normal vector for the data point according to the deviation. For example, if the deviation indicates a steeper curvature, computer 24 adjusts the normal vector to represent the steeper curvature. If the deviation indicates a flatter curvature, computer 24 adjusts the normal vector to represent the flatter curvature. The amount of adjustment can be determined from the design of system 10.

Computer 24 may determine the curvature at the surface points from the curvature values in any suitable manner. In certain embodiments, computer 24 determines the curvature at a surface point from an average of the one or more curvature values for the surface point. The average may be a weighted or unweighted average. For example, the average may be weighted by the quality of the image from each camera, where the value from a higher quality image has a greater weight than a value from a lower quality image. In certain embodiments, computer 24 determines applies a ray-tracing procedure to select a curvature value of the curvature values for the surface point, as described relative to FIGS. 5 and 6.

Computer 24 may output the topography of anterior corneal surface 16 via interface 25. The topography may be described in any suitable matter. For example, the topography may be described using a function, e.g., a biconic, aspheric, or Zernike polynomial-based function. As another example, the topography may be described using a map of the surface, e.g., an axial, tangential, refractive power, or elevation map.

Interface 25 and memory 34 may be as described below. Memory 34 stores data (e.g., image data 36) and applications (e.g., image analysis module 38). Image analysis module 38 may process image data 36 in any suitable manner. For example, image data 36 may be analyzed to identify landmark features of a part of eye 12, e.g., markings of an iris, that may be used to align images from different cameras.

Figure 2:
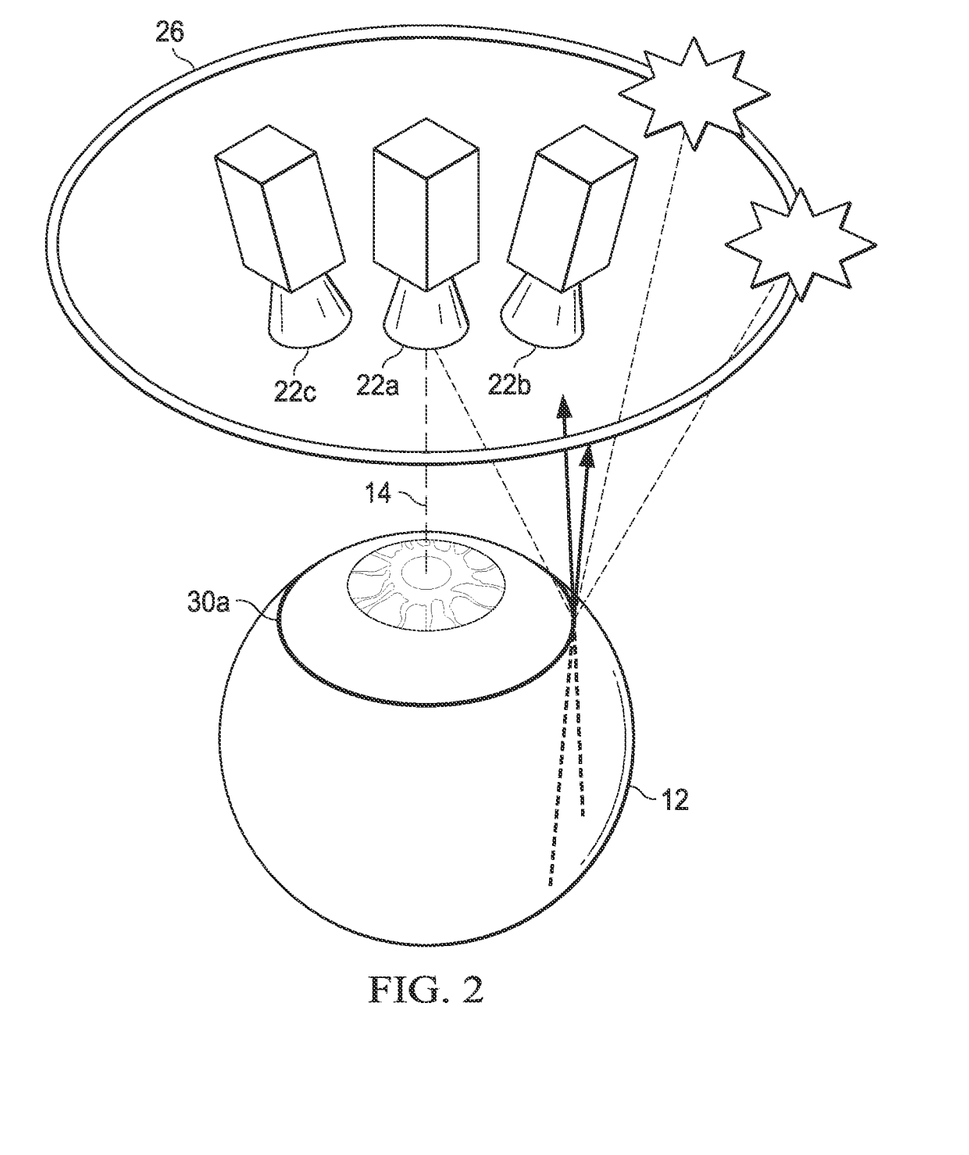
FIG. 2 illustrates an example of cameras detecting reflected rings.
Figure 3:
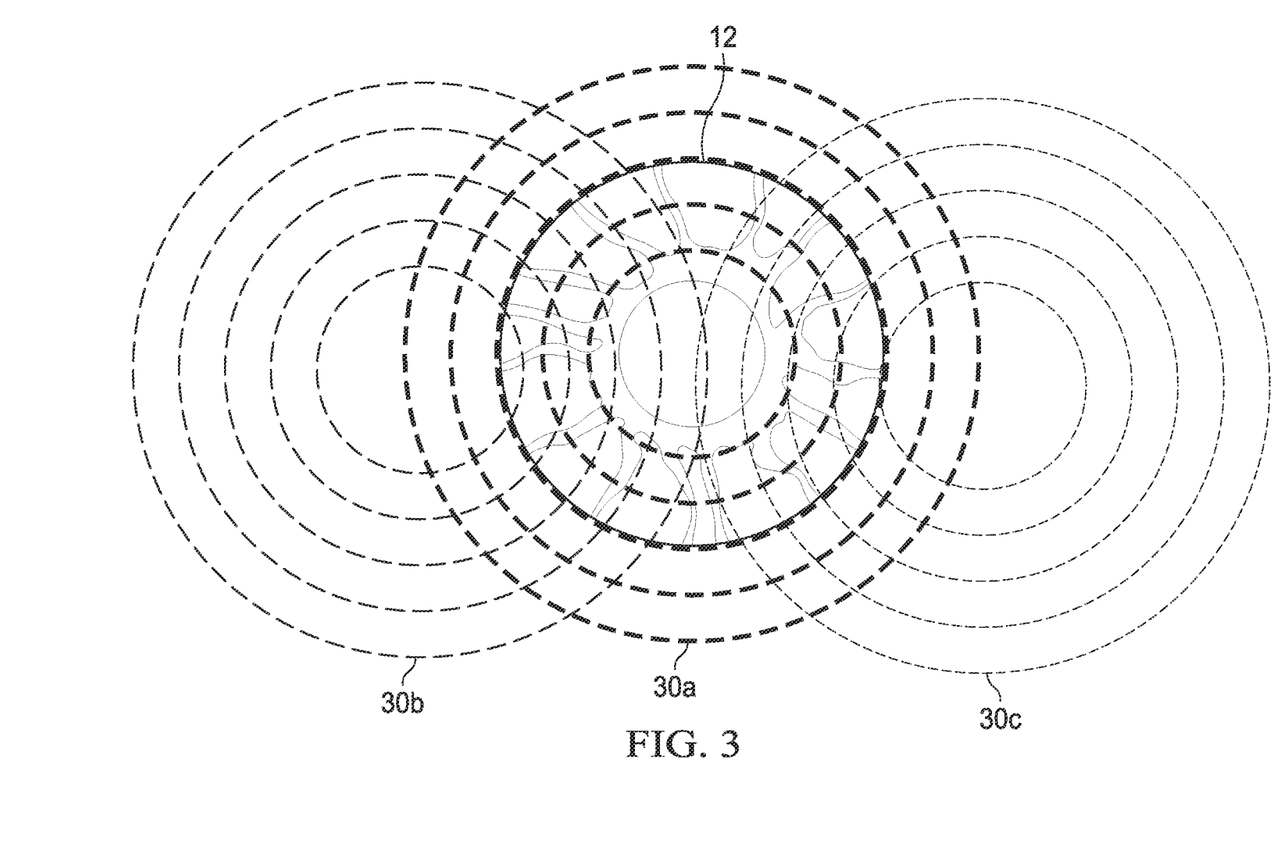
FIG. 3 illustrates coverage by the cameras.

FIGS. 2 and 3 illustrate how cameras 22 of system 10 may provide image data for determining the curvature of anterior corneal surface 16. FIG. 2 illustrates an example of cameras 22 (22a-22c) detecting reflected rings 30. FIG. 3 illustrates coverage by cameras 22: camera 22a captures the image of rings 30a; camera 22b captures the image of rings 30b; and camera 22c captures the image of rings 30c.

In certain embodiments, illuminator rings 26 illuminate rings 30 of a Placido pattern onto anterior corneal surface 16, which reflects rings 30. Cameras 22 detect the reflected rings 30. If a surface that reflects a ring 30 does not have any aberrations, the surface does not distort ring 30. The reflected ring 30 detected by camera 22 will have an expected shape, e.g., a shape that generally matches the shape of illuminator ring 30 prior to reflection. For example, if the illumination pattern comprises equally spaced rings (or dots or other shape), and if the surface is an ideal sphere, the reflected rings will be equally spaced.

If a surface that reflects ring 30 has an aberration, the reflected ring 30 detected by camera 22 may have a distortion that indicates the presence of the aberration. For example, if the illumination pattern comprises equally spaced rings (or dots or other shape), and if the surface has aberrations, areas where the reflected rings are closer together indicate that surface 16 has a steeper than spherical curvature, and areas where the rings are farther part indicate flatter curvature.

FIG. 2 shows detection by a camera 22a, which detects reflected ring 30a. Camera 22a provides images where the spacing between rings 30 may indicate an aberration in the meridional direction perpendicular to rings 30. However, camera 22a does not provide information about aberrations along the direction of a ring 30. Moreover, on-axis camera 22a cannot detect aberrations at or near axis 14.

As shown in FIG. 3, camera 22a captures the image of rings 30a; camera 22b captures the image of rings 30b; and camera 22c captures the image of rings 30c. Corneal coverage by multiple cameras 22 is greater than by one camera 22. Thus, system 10 can determine the shape of a greater area of anterior corneal surface 16. In addition, portions of anterior corneal surface 16 are covered by more than one camera 22. Thus, images from cameras 22 can provide indications of aberrations along more directions than images from a single camera 22. Moreover, off-axis cameras 22b, 22c can detect aberrations at or near axis 14. Accordingly, the cameras 22 of system 10 may provide improved image data for determining the curvature of anterior corneal surface 16.

Figure 4:
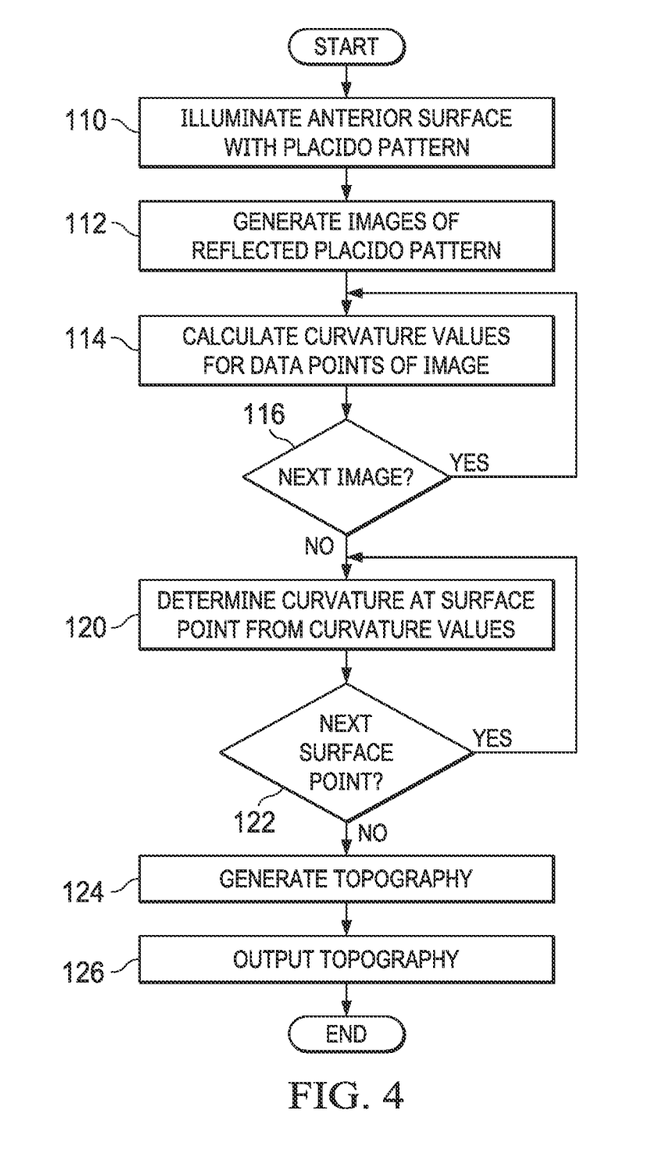
FIG. 4 illustrates an example of a method for generating a topography of an anterior corneal surface, which may be performed by the system of FIG. 1.

FIG. 4 illustrates an example of a method for generating a topography of an anterior corneal surface 16, which may be performed by system 10 of FIG. 1. In certain embodiments, computer 24 may perform certain steps by executing image analysis module 38 and by sending instructions to the components of system 10. The method starts at step 110, where illuminator 20 illuminates anterior corneal surface 16 with a Placido pattern. Anterior corneal surface 16 reflects the Placido pattern. Cameras 22 detect the reflected Placido pattern and generate images of the reflected Placido pattern at step 112. Cameras 22 provide the images to computer 24. The images may be provided as image data.

Computer 24 calculates a curvature value for the data points of an image for each image from cameras 22 at steps 114 and 116. Each data point corresponds to a surface point of at least a portion of anterior corneal surface 16. Computer 24 may calculate curvature values at step 114 in any suitable manner. In certain embodiments, computer 24 determines there is a deviation between the expected Placido pattern and the reflected Placido pattern at a data point, and adjusts the normal vector for the data point according to the deviation. If there is a next image from another camera at step 116, the method returns to step 114 to calculate curvature values for the next image. If there is no next image, the method proceeds to step 120.

Computer 24 determines the curvature at the surface points from the curvature values corresponding to the surface points at steps 120 and 122. Computer 24 may determine the curvature at step 120 in any suitable manner. In certain embodiments, computer 24 determines the curvature at a surface point from a function of one or more curvature values corresponding to the surface point. For example, computer 24 may take the average of the curvature values. In other embodiments, computer 24 applies a ray-tracing procedure to determine the curvature. If there is a next surface point of surface 16 at step 122, the method returns to step 120 to calculate curvature values for the next surface point. If there is no next surface point, the method proceeds to step 124.

Computer 24 generates a topography of anterior corneal surface 16 from the curvatures at the surface points at step 124. The curvatures at the surface points may be used to determine the shape of anterior corneal surface 16. For example, the curvatures may be the surface normals at the surface points, which can be used to generate the topography of surface 16. Computer 24 outputs the topography at step 126 via, e.g., interface 32. The method then ends.

Figure 5:
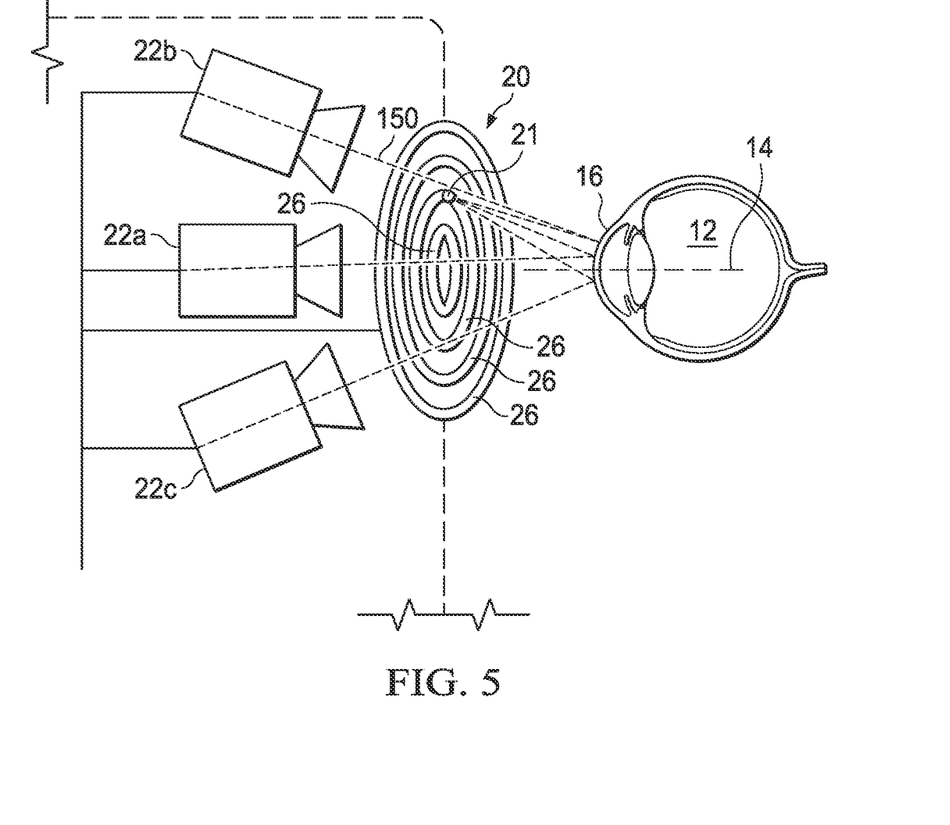
FIG. 5 illustrates an example of an environment where ray-tracing may be applied.
Figure 6:
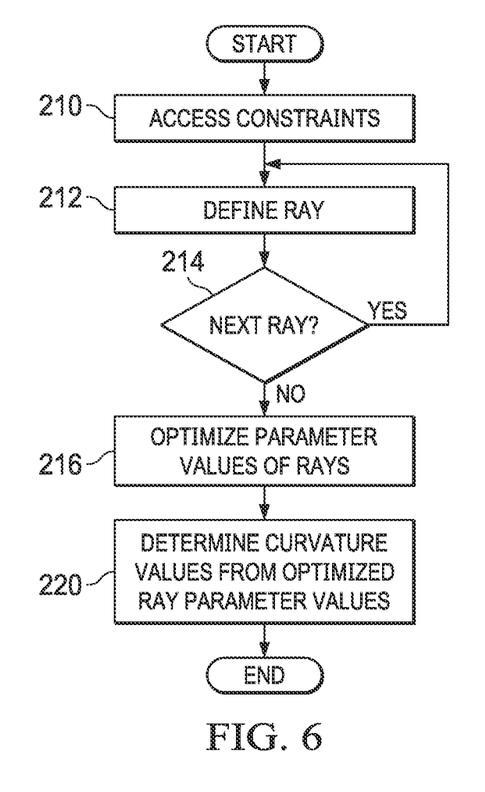

FIGS. 5 and 6 illustrate an example of a method for applying ray-tracing to determine the shape of anterior corneal surface 16, which may be performed by system 10 of FIG. 1. In certain embodiments, the method may be used to determine the curvature at the surface points, as described at steps 120 and 122 of FIG. 4.

FIG. 5 illustrates an example of an environment where ray-tracing may be applied. In the illustrated example, eye 12 has an anterior corneal surface 16. System 10 includes an illuminator 20 and cameras 22 (22a-22c). Illuminator 20 includes illuminator elements 21 that direct light rays 150 towards anterior corneal surface 16. (For simplicity, only one illuminator element 21 is shown). Cameras 22 detect reflected light rays 150 from anterior corneal surface 16.

Certain characteristics of the environment may be used as constraints to trace rays 150 to and from eye 12. Constraints may be determined from, e.g., general knowledge, arrangement of the components of system 10, position of eye 12 relative to system 10, previous measurements of eye 12, and/or images from cameras 22. For example, the relative distances and orientations among cameras 22, illuminator elements 21, and anterior corneal surface 16 may be determined from the arrangement of the components of system 10 and the position of eye 12 relative to system 10. As another example, an initial estimate of the shape of anterior corneal surface 16 may be determined from general knowledge, previous measurements of eye 12, and/or images from cameras.

FIG. 6 illustrates the example of the method for applying ray-tracing. In certain embodiments, computer 24 may perform the method by executing image analysis module 38 and by sending instructions to other components of system 10. According to an overview of the example, computer 24 defines rays 150 from illuminator elements 21, to anterior corneal surface 16, and to cameras 22. Computer 24 optimizes parameter values of rays 150 by determining values that optimize agreement among constraints. Computer 24 then determines curvature values that describe the shape of anterior corneal surface 16 from the optimized ray parameter values.

The method starts at step 210, where computer 24 accesses constraints for rays 150. Initially, the constraints may be given initial values that may be adjusted during optimization. For example, curvature values describing the shape of anterior corneal surface 16 may be given an initial estimated values.

Rays 150 are defined at steps 212 and 214 from illuminator elements 21, to anterior corneal surface 16, and to cameras 22. In certain embodiments, rays 150 are parameterized, i.e., expressed in terms of parameters that are assigned values. A ray 150 from an illuminator element 21 to a point of anterior corneal surface 16 can be determined from the position of an illuminator element 21 relative to eye 12. "Position" may refer to the location of an object (e.g., location of the object in x, y, z, space) and/or the orientation of the object (e.g., direction in which the object is pointing). A ray 150 from a point of anterior corneal surface 16 to a point of camera 22 (e.g., point of image plane of camera 22a) an illuminator element 21 can be determined from the position of camera 22 relative to eye 12. An anterior angle by which a point of anterior corneal surface 16 reflects ray 150 can be calculated from the initial estimate of the curvature of anterior corneal surface 16 at the point.

If there is a next ray 150 at step 214 to define, the method returns to step 212 to define the next ray 150. The number of rays may vary depending on the illumination pattern. In certain embodiments, a ray may be defined for each illuminator element (e.g., an illuminator point source) per camera, e.g., $10^2$ to $10^3$ rays per Placido ring per camera. Rays 150 from different images may be aligned by identifying rays 150 traced to the same feature of eye 12.

Parameter values of rays 150 are optimized at step 216 by determining values for the parameters that optimize the agreement among the constraints. For example, computer 24 may determine values that minimize residuals, i.e., the difference between the observed value and the parameter value. Any suitable optimization technique may be used, e.g., the least squares or random sample consensus (RANSAC) method.

Curvature values that describe the shape of anterior corneal surface 16 are determined from the optimized ray parameter values at step 220. For example, the optimized ray parameter values may adjust the path of a ray 150 reflected by anterior corneal surface 16 such that the reflection angle is also adjusted. The adjusted reflection angle may be used to adjust the normal line of surface 16. The method then ends.

A component (such as computer 24) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic system for generating a topography of an anterior corneal surface of an eye, the system comprising:
   an illuminator configured to illuminate the anterior corneal surface of the eye with a Placido pattern, the eye having an axis, the anterior corneal surface reflecting the Placido pattern;
   a plurality of cameras, each camera configured to generate an image of the reflected Placido pattern to yield a plurality of images, at least one camera oriented off the axis of the eye; and
   a computer configured to:
      receive the plurality of images from the cameras;
      for each image of the plurality of images, calculate a curvature value for each data point of a plurality of data points of the image, each data point of the image corresponding to a surface point of a plurality of surface points of the anterior corneal surface, the calculations yielding a plurality of curvature values for each surface point of the plurality of surface points, wherein the curvature value for a data point is a normal vector, the normal vector representing a surface normal at the surface point corresponding to the data point;
      for each surface point of the plurality of surface points, determine the curvature at the surface point from one or more curvature values for the surface point; and
      generate the topography of the anterior corneal surface from the curvatures at the surface points of the anterior corneal surface.

2. The ophthalmic system of claim 1, the computer configured to, for each image of the plurality of images, calculate the curvature value for each data point by:
   determining there is a deviation between an expected Placido pattern and the reflected Placido pattern at the data point; and
   adjusting the normal vector for the data point according to the deviation.

3. The ophthalmic system of claim 1, the computer configured to, for each image of the plurality of images, calculate the curvature value for each data point by:
   determining there is a deviation between an expected Placido pattern and the reflected Placido pattern at the data point; and
   performing at least one of:
   if the deviation indicates a steeper curvature, adjusting the normal vector for the data point to represent the steeper curvature; and
   if the deviation indicates a flatter curvature, adjusting the normal vector for the data point to represent the flatter curvature.

4. The ophthalmic system of claim 1, the computer configured to, for each surface point of the plurality of surface points, determine the curvature at the surface point from one or more curvature values for the surface point by:
   determining the curvature at the surface point from a function of the curvature values for the surface point.

5. The ophthalmic system of claim 4, the computer configured to determine the curvature at the surface point from the function of the curvature values for the surface point by:
   determining the curvature at the surface point from an average of the curvature values for the surface point.

6. The ophthalmic system of claim 4, the computer configured to determine the curvature at the surface point from the function of the curvature values for the surface point by:
   determining the curvature at the surface point from a weighted average of the curvature values for the surface point.

7. The ophthalmic system of claim 1, the computer configured to, for each surface point of the plurality of surface points, determine the curvature at the surface point from one or more curvature values for the surface point by:
   applying a ray-tracing procedure to determine the curvature at the surface point.

8. The ophthalmic system of claim 7, the computer configured to apply the ray-tracing procedure to determine the curvature at the surface point by:
   defining a plurality of rays, each ray described by a plurality of ray parameters, each ray parameter having a value;
   optimizing the values of the ray parameters according to a plurality of constraints, the constraints comprising the curvature values for the surface points; and
   determining the curvature at a surface point from the optimized values of the ray parameters.

9. The ophthalmic system of claim 7, the computer configured to apply the ray-tracing procedure to determine the curvature at the surface point by:
defining a plurality of rays, each ray traced from an illuminator element of the illuminator, to the anterior corneal surface, and to a camera of the plurality of cameras, each ray described by a plurality of ray parameters, each ray parameter having a value;
optimizing the values of the ray parameters according to a plurality of constraints, the constraints comprising the curvature values for the surface points; and
determining the curvature at a surface point from the optimized values of the ray parameters.

10. A method for generating a topography of an anterior corneal surface of an eye, the method comprising:
illuminating, by an illuminator, the anterior corneal surface of the eye with a Placido pattern, the eye having an axis, the anterior corneal surface reflecting the Placido pattern;
generating, by a plurality of cameras, a plurality of images of the reflected Placido pattern, at least one camera oriented off the axis of the eye;
receiving, by a computer, the plurality of images from the cameras;
for each image of the plurality of images, calculating, by the computer, a curvature value for each data point of a plurality of data points of the image, each data point of the image corresponding to a surface point of a plurality of surface points of the anterior corneal surface, the calculations yielding a plurality of curvature values for each surface point of the plurality of surface points, wherein the curvature value for a data point is a normal vector, the normal vector representing a surface normal at the surface point corresponding to the data point;
for each surface point of the plurality of surface points, determining, by the computer, the curvature at the surface point from one or more curvature values for the surface point; and
generating, by the computer, the topography of the anterior corneal surface from the curvatures at the surface points of the anterior corneal surface.

11. The method of claim 10, for each image of the plurality of images, calculating, by the computer, the curvature value for each data point by:
determining there is a deviation between an expected Placido pattern and the reflected Placido pattern at the data point; and
adjusting a normal vector for the data point according to the deviation.

12. The method of claim 10, for each image of the plurality of images, calculating, by the computer, the curvature value for each data point by:
determining there is a deviation between an expected Placido pattern and the reflected Placido pattern at the data point; and
performing at least one of:
if the deviation indicates a steeper curvature, adjusting the normal vector for the data point to represent the steeper curvature; and
if the deviation indicates a flatter curvature, adjusting the normal vector for the data point to represent the flatter curvature.

13. The method of claim 10, for each surface point of the plurality of surface points, determining, by the computer, the curvature at the surface point from one or more curvature values for the surface point by:
determining the curvature at the surface point from a function of the curvature values for the surface point.

14. The method of claim 13, determining, by the computer, the curvature at the surface point from the function of the curvature values for the surface point by:
determining the curvature at the surface point from an average of the curvature values for the surface point.

15. The method of claim 13, determining, by the computer, the curvature at the surface point from the function of the curvature values for the surface point by:
determining the curvature at the surface point from a weighted average of the curvature values for the surface point.

16. The method of claim 10, for each surface point of the plurality of surface points, determining, by the computer, the curvature at the surface point from one or more curvature values for the surface point by:
applying a ray-tracing procedure to determine the curvature at the surface point.

17. The method of claim 16, applying, by the computer, the ray-tracing procedure to determine the curvature at the surface point by:
defining a plurality of rays, each ray traced from an illuminator element of the illuminator, to the anterior corneal surface, and to a camera of the plurality of cameras, each ray described by a plurality of ray parameters, each ray parameter having a value;
optimizing the values of the ray parameters according to a plurality of constraints, the constraints comprising the curvature values for the surface points; and
determining the curvature at a surface point from the optimized values of the ray parameters.

18. An ophthalmic system for generating a topography of an anterior corneal surface of an eye, the system comprising:
an illuminator configured to illuminate the anterior corneal surface of the eye with a Placido pattern, the eye having an axis, the anterior corneal surface reflecting the Placido pattern;
a plurality of cameras, each camera configured to generate an image of the reflected Placido pattern to yield a plurality of images, at least one camera oriented off the axis of the eye; and
a computer configured to:
receive the plurality of images from the cameras;
for each image of the plurality of images, calculate a curvature value for each data point of a plurality of data points of the image, each data point of the image corresponding to a surface point of a plurality of surface points of the anterior corneal surface, the calculations yielding a plurality of curvature values for each surface point of the plurality of surface points, the curvature value for a data point is a normal vector, the normal vector representing a surface normal at the surface point corresponding to the data point, a curvature value calculated for each data point by:
determining there is a deviation between an expected Placido pattern and the reflected Placido pattern at the data point; and
performing at least one of:
if the deviation indicates a steeper curvature, adjusting a normal vector for the data point to represent the steeper curvature; and
if the deviation indicates a flatter curvature, adjusting the normal vector for the data point to represent the flatter curvature;

for each surface point of the plurality of surface points, determine the curvature at the surface point from one or more curvature values for the surface point, the curvature at the surface point determined from a weighted average of the curvature values for the surface point or by applying a ray-tracing procedure to determine the curvature at the surface point; and
generate the topography of the anterior corneal surface from the curvatures at the surface points of the anterior corneal surface.

* * * * *